(12) United States Patent
Toniolo

(10) Patent No.: US 10,975,401 B2
(45) Date of Patent: Apr. 13, 2021

(54) BIOTECHNOLOGICAL METHOD FOR THE PRODUCTION OF ACRYLAMIDE AND NEW BACTERIAL STRAIN

(71) Applicant: COLUMBIA S.R.L., Monticello Conte Otto (IT)

(72) Inventor: Stefano Toniolo, Monticello Conte Otto (IT)

(73) Assignee: Columbia S.R.L., Monticello Conte Otto (VI) (IT)

( * ) Notice: Subject to any disclaimer, the term of this patent is extended or adjusted under 35 U.S.C. 154(b) by 152 days.

(21) Appl. No.: 16/096,227

(22) PCT Filed: May 18, 2017

(86) PCT No.: PCT/IB2017/052937
§ 371 (c)(1),
(2) Date: Oct. 24, 2018

(87) PCT Pub. No.: WO2017/199200
PCT Pub. Date: Nov. 23, 2017

(65) Prior Publication Data
US 2019/0127768 A1 May 2, 2019

(30) Foreign Application Priority Data
May 18, 2016 (IT) .................. 102016000051247

(51) Int. Cl.
*C12P 13/02* (2006.01)
*C12R 1/01* (2006.01)
*C12N 1/20* (2006.01)
*C12R 1/365* (2006.01)

(52) U.S. Cl.
CPC .............. *C12P 13/02* (2013.01); *C12N 1/20* (2013.01); *C12R 1/01* (2013.01); *C12R 1/365* (2013.01); *C12Y 402/01084* (2013.01)

(58) Field of Classification Search
CPC . C12P 13/02; C12R 1/01; C12R 1/365; C12Y 402/01084; C12N 1/20; C12N 9/88; A62D 2101/20; A62D 3/02; C07K 14/195
See application file for complete search history.

(56) References Cited

U.S. PATENT DOCUMENTS

| | | | |
|---|---|---|---|
| 5,827,699 A | 10/1998 | Yanenko et al. | |
| 2004/0142447 A1 | 7/2004 | Robins et al. | |
| 2013/0035232 A1* | 2/2013 | Pierce | C12N 9/96 504/117 |

FOREIGN PATENT DOCUMENTS

| | | |
|---|---|---|
| EP | 2 749 637 A1 | 7/2017 |
| WO | 2002/055670 A1 | 7/2002 |
| WO | 2003/066800 A2 | 8/2003 |
| WO | 2016/050819 A1 | 4/2016 |

OTHER PUBLICATIONS

Keith A. Powell et al., *Directed Evolution and Biocatalysis*, Angewandte Chemie International Edition, Wiley-VCH Verlag GMBH, vol. 40, No. 21, Nov. 5, 2001, pp. 3948-3959. XP001111701.
Xiaomei Su et al., *Rhodococcus biphenylivorans sp. nov., a Polychlorinated Biphenyl-Degrading Bacterium*, Antonie Van Leeuwenhock, vol. 107, No. 1, Oct. 15, 2014, pp. 55-63. XP035418033.
Xiaomei et al., *Identification, Characterization and Molecular Analysis of the Viable but Nonculturable Rhodococcus biphenylivorans*, Scientific Reports, vol. 5, Dec. 21, 2015, pp. 18590. XP055329682.
International Search Report and Written Opinion dated Aug. 29, 2017, issued in PCT Application PCT/IB2017/052937, filed May 18, 2017.

\* cited by examiner

*Primary Examiner* — Deborah K Ware
(74) *Attorney, Agent, or Firm* — Workman Nydegger

(57) ABSTRACT

A bacterial strain of *Rhodococcus biphenylivorans* named Palladio 22 and registered at the BCCM-LMG Bacteria Collection under registration number LMG P-29520. A method is provided for the production of acrylamide following hydration of acrylonitrile using a biomass of the bacterial strain.

14 Claims, No Drawings

BIOTECHNOLOGICAL METHOD FOR THE PRODUCTION OF ACRYLAMIDE AND NEW BACTERIAL STRAIN

BACKGROUND OF THE INVENTION

Field of the Invention

The present invention relates to a bacterial strain belonging to the *Rhodococcus biphenylivorans* species, which has the ability to develop the nitrile hydratase enzyme.

The invention also relates to the method of culturing the bacterial strain, to the use of a biomass of this bacterial strain for the production of acrylamide by hydration of acrylonitrile, and to the corresponding acrylamide production method.

Prior Art

Acrylamide is an intermediate chemical compound in the synthesis of acrylates and is commonly used as a monomer for the production of various polymers and in the treatment as coagulant or flocculant of water supply or drainage water. In molecular biology, in the form of gel, acrylamide is used as a means of resolution and separation of proteins in chromatographic and electrophoretic techniques.

The polymerization is carried out in aqueous solution and the polymer is characterized by high solubility in water and insolubility in common organic solvents.

Acrylamide still today in some plants is produced by chemical hydration of acrylonitrile by sulfuric acid and in the presence of reduced copper as a catalyst.

However, chemical hydration reactions have numerous problems including the complexity in the preparation of the metallic catalyst, the difficulty in recovering and purifying the acrylamide formed, the formation of secondary products, a low yield of conversion and strict reaction conditions.

In addition, the current industrial processes for the production of acrylamide include many different processing steps, resulting in increased raw material final costs.

It is therefore strongly felt that this compound should be derived from alternative sources that overcome all of the adverse events described while maintaining low production costs.

Enzymatic catalysis for conducting chemical reactions using biocatalysts such as microorganisms is well documented in the literature.

In the 1970s, the ability of some microorganisms to convert nitriles into the corresponding amides was described in the literature.

This conversion is catalyzed by a biocatalyst, the nitrile hydratase enzyme, synthesized by a variety of microorganisms belonging to different taxonomic groups, such as *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia, Rhodococcus* and *Comomonas*.

Patent document EP 2749637 A1 (US 20140187818) is known, which describes the bacterial strain *Rhodococcus aetherivorans* VKM Ac-2610D, which produces the nitrile hydratase enzyme necessary for converting acrylonitrile into acrylamide.

A drawback lies in that the bacterial strain *Rhodococcus aetherivorans* VKM Ac-2610D has an acrylamide production capacity by the nitrile hydratase enzyme not greater than 49%.

Patent document U.S. Pat. No. 5,827,699 discloses a new bacterial strain of *Rhodococcus rhodochrous* M33 VKM Ac-1515D, which possesses a high nitrile hydratase activity able to hydrate aliphatic and aromatic compounds to the corresponding amides.

This bacterial strain does not require the presence of any enzymatic inducer in the culture medium, where only salts, a carbon source (glucose, pyruvate or acetate) and a nitrogen source (ammonium, urea or nitrate salts) are present.

Disadvantageously, despite the fact that this bacterial strain possesses a constitutive nitrile hydratase activity and grows in the absence of inducers in the culture medium, the maximum amount of acrylamide produced in solution does not exceed 46% (weight/volume).

Most of the strains known today and used for the production of acrylamide are capable of producing a maximum concentration of acrylamide generally not greater than 40% (weight/weight) and consequently their use is limited.

In addition, disadvantageously, the components of the culture medium of the microorganisms required for growth, such as vitamins, yeast extract and peptone, are very expensive.

Although important studies have been conducted on the enzymatic hydrolysis process of nitriles and amides with the achievement of significant successes, the demand for finding new bacterial strains that produces nitrile hydratase is constantly growing.

This is partly due to the ecological safety and effectiveness of the biotechnological production of amides, partly due to the high cost of patented bacterial strains. Therefore, new microorganisms that produce this enzyme have been isolated in recent years.

Ultimately, the need to obtain a production of pure acrylamide without contaminating residues and capable of ensuring reproducible results has led researchers to seek new bacterial strains and develop alternative strategies to those indicated above.

DETAILED DESCRIPTION OF THE PREFERRED EMBODIMENTS

The object of the present invention is to provide a bacterial strain of the *Rhodococcus* genus provided with technological features that allow increasing the yield of the nitrile hydratase enzyme in the hydration reaction of a nitrile group into an amide group for the production of acrylamide, with respect to the bacterial strains described in the prior art.

A further object is the development of an improved, effective and rapid culture protocol for obtaining a high amount of biomass of the *Rhodococcus* strain, where by biomass it is meant the total mass of *Rhodococcus* cells present in the culture broth. The developed method allows obtaining a biomass per liter of culture broth greater than 100 g/L of biomass having a dry residue at 105° C. of about 25 g/L.

Moreover, the present invention relates to methods of producing high concentrations of acrylamide, with the further object of significantly reducing the unnecessary costs of bacterial strain culture with respect to known manufacturing methods.

The foregoing objects are achieved by the bacterial strain as characterized in claim 1, and specifically by a strain of *Rhodococcus biphenylivorans* named "Palladio 22", which was registered and deposited as a biological material under the Budapest Treaty on Dec. 4, 2016 at the Belgian Coordinated Collections of Microorganisms—Laboratorium voor Microbiologie Universiteit Gent (BCCM-LMG) located at K. L. Ledeganckstraat 35, B-9000 Gent, Belgium and assigned Accession Number LMG P-29520.

The above bacterial strain produces the nitrile hydratase enzyme. The above identified bacterial strain preferably is in the form of dried, lyophilized or paste biomass having a dry residue at 105° C. from 18 to 30%, preferably from 20 to 27%.

The present invention relates to the use of said bacterial strain for the production of chemical compounds, preferably amides. The present invention relates to the use of said bacterial strain for the production of acrylamide.

An object of the invention is also a method for the production of acrylamide by hydration of acrylonitrile using a biomass of the above bacterial strain, wherein the hydration process takes place at a concentration of acrylonitrile smaller than 0.8% of the total weight of the reaction solution.

Preferably, acrylonitrile is added to an aqueous solution containing the biomass of the bacterial strain so that, during the hydration process, the concentration of free acrylonitrile in solution is never greater than 0.8% of the total weight of the reaction solution.

Preferably, the method described has a yield of acrylamide production of between 50% and 57.5%, preferably between 50 and 54% (weight/weight). Preferably, the production of acrylamide takes place in a temperature range of between 14 and 23° C. and a pH between 5.0 and 8.5 under stirring.

The invention further relates to a method for the production of acrylamide following hydration of acrylonitrile using a biomass of said bacterial strain wherein the biomass is immobilized on a solid substrate.

An object of the invention is also a method for the production of acrylamide following hydration of acrylonitrile using the nitrile hydratase enzyme extracted from a biomass of the bacterial strain in which the enzyme is immobilized on a solid substrate.

The invention further relates to a culture method of the above bacterial strain, wherein the growth of the bacterial strain comprises the inoculation of the strain in a nutrient medium comprising: a phosphate buffer solution comprising sodium and potassium, a carbon source, a nitrogen source, a magnesium salt, a zinc salt, a calcium salt, an iron salt (II), a cobalt salt and, optionally, a yeast extract. Preferably, the growth takes place at a temperature of 10-35° C., preferably 20-35° C., for 2-4 days at a growth pH of between 8.3-6.3, preferably 7.4 and 6.5.

Preferably, the culture method further comprises: a step of growing the strain in a further solid medium, a step of growing the strain in a liquid medium, a fermentation step, a step of flocculation and separation of the biomass of the bacterial strain.

Preferably, the bacterial strain is cultured until the cells have an optical density of between 90-220 OD measured at a 540 nm wavelength in a cell having a thickness of 10 mm.

Preferably, the resulting bacterial strain has a nitrile hydratase activity of at least 150 μmoles of amide/min/mg dry weight cells.

Moreover, the invention also relates to bacterial strains of *Rhodococcus biphenylivorans* obtained by reproduction or multiplication of the bacterial strain of the invention.

In particular, the bacterial strain of the invention is able to hydrate the acrylonitrile substrate to acrylamide, allowing a final product output greater than the bacterial strains described in the prior art.

Such a high production of acrylamide is afforded by the advantageous resistance of the strain to the toxicity of acrylamide.

In fact, the Applicant has surprisingly found that the bacterial strain object of the invention can tolerate and achieve acrylamide concentrations during the conversion reaction greater than 50% (weight/weight).

The bacterial strain producer of acrylamide was isolated from Italian soil by sampling on soils where grassy/leafy material in decomposition was present.

Isolation and culture of the strain took place with the use of culture media and analytical methods capable of selecting microorganisms capable of producing the nitrile hydratase enzyme, an enzyme that allows the hydration of nitrile groups to the corresponding amides.

The bacterial strain object of the invention was identified by sequencing a region of 1365 nucleotides of the ribosomal RNA 16S (16S rRNA) coding gene.

The sequence obtained showed a similarity of 99.93% with the strain of the *Rhodococcus biphenylivorans* (TG9$^T$) species with a single nucleotide of difference compared to the total length of the comparable sequence.

The bacterial strain object of the invention has the following morphological and biochemical characteristics:
  agar culture: glossy, pink-orange colonies and circular and convex morphology;
  mobility: no;
  spore-forming: no;
  Gram stain: positive;
  culture conditions: 20-35° C. in aerobiosis.

The bacterial strain of the invention is aerobic, catalase positive and, depending on the growth phases, has a stick or coconut morphology under microscopy.

The *Rhodococcus biphenylivorans* Palladio 22 bacterial strain has excellent growth characteristics and is capable of catalyzing the hydrolysis of aliphatic and aromatic nitriles in the corresponding amide.

Such hydration action is specifically catalyzed by the nitrile hydratase enzyme and is preferably induced by the addition of an enzyme inducer to the culture medium, such as urea and derivatives thereof.

The bacterial strain object of the invention was characterized from a functional point of view; by PCR amplification and sequencing by Sanger method, it was seen that the strain possesses α and β subunits of the Cobalt-dependent nitrile hydratase enzyme.

Another advantageous feature of the strain is that it has a very low amidasic activity, thus guaranteeing an excellent quality of the acrylamide produced. The amidasic activity in fact involves the degradation of the acrylamide produced.

Advantageously, the bacterial strain of *Rhodococcus biphenylivorans* Palladio 22 grows in a simple culture medium that does not contain expensive nutrients such as vitamins, and other growth factors.

In other words, the Applicant has found that the hydratase activity of the bacterial strain of the invention is improved with respect to the bacterial strains described in the prior art, under standard culture conditions, in suitably formulated culture media.

The use of ad hoc culture media allows their formulation by the combination of the individual components, not only providing economic saving over the use of commercially available ready-to-use media, but also the possibility of modulating, depending on the specific needs, the concentration of each component.

Unlike what currently available to date, the bacterial strain of the invention has the ability to withstand very high concentrations of acrylamide, produced and released in the culture medium, and this makes it advantageously suitable for high-concentration acrylamide industrial production.

In particular, it was found that the *Rhodococcus biphenylivorans* Palladio 22 strain has a surprising resistance to acrylamide concentrations significantly greater than 50% (weight/weight).

Such features of the bacterial strain and features of the production method make the invention described economically advantageous and industrially applicable with success.

The present invention also relates to the synthesis process developed for the large-scale production of acrylamide based on the use of a biomass of the bacterial strain and on the subsequent separation of acrylamide from the biomass itself.

The growth of the *Rhodococcus biphenylivorans* Palladio 22 strain takes place in a first step (e.g., growth in Petri dishes and slant agar tubes) by inoculum in a solid nutrient medium, generally agarized, while in the subsequent propagation steps (e.g., flask and fermenter) it is conducted in a liquid nutrient medium (culture broth).

The solid nutrient medium consists of bovine extract, pepton, NaCl, yeast extract and agar. The liquid nutrient medium contains carbon sources, nitrogen and mineral salts.

In general, in the liquid medium, the carbon source that can be assimilated consists of one or more sugars alone or in a mixture. Preferably, the carbon source is selected from glucose, cellobiose, fructose, galactose, maltose, mannose, sucrose, ribose, glycerol, mannitol, sorbitol, salicin, inulin, citrate, pyruvate, succinate, fumarate and combinations thereof.

Typically, the concentration of sugar in the liquid medium is of between 20 and 80 g/L according to the amount of biomass to be obtained and depending on the specific growth step.

Typically, in the liquid medium, the nitrogen source is of between 3 and 25 g/L. The nitrogen source preferably used is urea.

In a preferred embodiment, cobalt ion is used in the liquid medium as an inducer for the synthesis of the active nitrile hydratase enzyme at a concentration of between 0.01 and 0.08 g/L.

In the formulation of the liquid culture medium, moreover, various salts selected from those present in the common nutrient media used for the culture of microorganisms may also be employed.

Non-limiting examples of such salts are phosphates, sulfates, chlorides, potassium, ammonium, cobalt, calcium and magnesium.

Preferably, the liquid nutrient medium comprises a carbon source, a nitrogen source, mineral salts and yeast extract.

In a preferred embodiment, the first growth step of the bacterial strain takes place in a solid nutrient medium, preferably on Petri dishes filled with culture medium made from bovine extract, pepton, NaCl, yeast extract and agar, preferably at 1.5% to allow gelification thereof. The culture medium is usually sterilized at 121° C. for 15-20 minutes in autoclave.

The solid nutrient medium is preferably inoculated with the *Rhodococcus biphenylivorans* Palladio 22 strain on the whole surface, using a sterile loop.

The strain growth takes place at a temperature of 20-35° C., preferably 28-32° C., for 2-5 days, preferably 3-4 days, at a growth pH of between 7.4 and 6.5.

Macroscopically, it is possible to verify the growth progress by the appearance of visible colonies having a circular and convex shape, with the typical pink-orange color.

The next step involves the seeding of the bacterial strain, preferably in slant agar tubes having the characteristic of having the medium suitably solidified to obtain an inclined surface.

These tubes contain the same culture medium of the Petri dishes and are subjected to the sterilization process as described above.

Seeding in the slants tubes takes place by taking the colonies from the Petri dishes and seeding the cells taken on the inclined surface of the slants, preferably by using a sterile loop.

The growth of the bacterial strain in the slant tubes is carried out in an incubator at a temperature of 20-35° C., preferably 28-32° C., and for a period of 1-4 days, preferably 2-3 days.

At the end of the growth of the colonies, the biomass grown on the slant is resuspended, preferably with a vortex, in sterile saline having a neutral pH of 6.5-7.5 and a temperature of between 10 and 35° C., preferably at a pH of 7.0±0.2 and a temperature of between 15 and 25° C.

The suspension of the bacterial strain thus prepared is subsequently inoculated into a glass flask containing either a generic liquid medium, preferably supplemented with a yeast extract at a concentration of 10-20 g/L, or a synthetic medium containing sugar, urea, phosphates, sulfates, chlorides, potassium, ammonium, cobalt, calcium, magnesium, iron and yeast extract.

Preferably, the bacterial strain suspension is used for the inoculation of a flask containing a generic liquid medium supplemented with yeast extract at a concentration of 10-20 g/L, or in a synthetic medium having the following composition (g/L):

| | |
|---|---|
| $Na_2HPO_4 \times 12\ H_2O$ | 4.7-5.4 |
| $KH_2PO_4$ | 1.4-1.6 |
| Urea | 5-11 |
| Sugar | 15-25 |
| $CoCl_2 \times 6\ H_2O$ | 0.01-0.02 |
| $MgSO_4 \times 7\ H_2O$ | 0.85-1.0 |
| $ZnSO_4 \times 7\ H_2O$ | 0.08-0.4 |
| $Ca^{2+}$ salt | 0.1-0.4 |
| $FeSO_4 \times 7H_2O$ with chelating agent | 0.02-0.045 |
| Yeast extract | 3-10 |
| Demineralized water | at 1 L |

The bacterial strain object of the invention is aerobic and, in the liquid medium, it grows under stirring by means of an orbital shaker at 200-350 rpm, preferably about 300 rpm. By promoting the oxygenation of the culture medium, stirring allows a greater yield of bacterial growth and consequently a greater production of the nitrile hydratase enzyme.

The bacterial growth in flask takes place at a temperature of 20-35° C., preferably between 28 and 32° C., pH 6.3-8.3, preferably ≤6.5 and ≥7.4 until reaching an optical density of 30-40 OD of the cell suspension, measured at a wavelength of 540 nm in a cuvette with a thickness of 10 mm.

It is necessary to stop the bacterial growth in flask preferably at a value of 35-38 OD, indicating that the cells are in a high number and are about to enter the stationary growth phase.

Obtaining a high OD value during the growth of the bacterial strain in the flask allows having cells still in active growth, advantageously promoting the reduction of time required for the next growth scale-up step in the fermenter.

The resulting bacterial suspension is used for subsequent inoculation in a first fermenter.

In this fermenter, a volume of 1/50 of the final volume of the fermentation broth is preferably inoculated. For example, if the fermenter has a useful working volume of 20 L, 400 mL of cell suspension are inoculated.

In a preferred embodiment, the bacterial growth in the fermenter with a working volume of 20 L takes place under particular conditions:
- aeration: the fermenter is flushed by sterile air, for example by means of a sparger placed on the bottom of the fermenter; the initial aeration conditions range from 5 L/min to 10 L/min;
- pressure: inside the fermenter there must be a slightly positive pressure so as to contribute to a better absorption of oxygen in the culture broth. The relative internal pressure is of between 0.1 and 0.3 bar, preferably between 0.15 and 0.25 bar;
- stirring: initially, the stirring inside the reactor is slow and may vary depending on the size and shape of the stirrers and the size of the fermenter. Generally, the initial stirring values in a small reactor are 150 to 500 rpm. In the initial growth condition, the stirring rpm range from 200 to 250 rpm; stirring varies in such a way as to maintain an optimal oxygen concentration ($\leq 55\%$) at any time;
- temperature: throughout the fermentation time, it is maintained constant at 20-35° C., preferably between 28 and 32° C.
- pH: ranges between 6.0 and 8.0, preferably between 6.5 and 7.4, and corrections for maintaining it at optimal values are carried out by adding NaOH or $H_3PO_4$;
- $pO_2$: the parameter that measures the $pO_2$ is very important for the success of fermentation and may range between values of $\leq 55\%$ up to 100%. Since the bacterial strain of the invention is aerobic, there is a directly proportional relationship between the bacterial concentration and the oxygen demand in the culture broth.

In such culture conditions, the aerobic microbial growth produces high levels of foam, and this phenomenon worsens as the rate of growth and concentration of bacteria increases. In fact, if the foam level is not checked with appropriate level probes and anti-foaming agents, it can grow up to clogging the fermenter outlet filter or even leak from the fermenter.

Preferably, a culture medium having the following composition (g/L) is used in a fermenter:

| | |
|---|---|
| $Na_2HPO_4 \times 12\ H_2O$ | 4.7-5.4 |
| $KH_2PO_4$ | 1.4-1.6 |
| Urea | 10-25 |
| Sugar | 30-80 |
| $CoCl_2 \times 6\ H_2O$ | 0.035-0.08 |
| $MgSO_4 \times 7\ H_2O$ | 0.85-1.2 |
| $ZnSO_4 \times 7\ H_2O$ | 0.08-0.4 |
| $CaCl_2 \times 2\ H_2O$ or $Ca^{2+}$ salt | 0.2-0.6 |
| $FeSO_4 \times 7H_2O$ with chelating agent | 0.02-0.05 |
| Anti-foaming agent | 0.5-2.5 |
| Yeast extract | 3-20 |
| Demineralized water | at 1 L |

Advantageously, in order to obtain a high bacterial concentration, a fed-batch fermentation process may be employed in which the nutrient(s) is/are injected into small amounts at a time.

Controlled bacterial growth in the fermenter is stopped upon reaching the optical density of 90-220 OD, preferably between 140 and 180 OD measured at a wavelength of 540 nm in a cell having a thickness of 10 mm according to known methods.

The new bacterial strain object of the present invention, according to the growth process described above, is capable of producing the nitrile hydratase enzyme having a specific activity measured by a spectrophotometric method, preferably equal to at least 150 μmoles of amide/min/mg of dry weight cells. The reaction for measuring the activity takes place in tubes with a maximum volume of 5-10 mL. The tubes are placed in a controlled-temperature water bath and stirred. The tubes are filled with an aqueous suspension of biocatalyst at known concentration, the latter is contacted with a known amount of reaction substrate (acrylonitrile) and is allowed to react for a given time. The reaction is blocked by the use of an acid; the concentration of acrylamide produced is then measured by known means, such as spectrophotometer, gas chromatograph or HPLC. Once the concentration of acrylamide produced is measured, the activity is calculated.

In the scale-up steps, the growth process maintains the same growth characteristics, with the only difference being that larger fermenters, 400/1000 L and 20000/50000 L, are used.

At the end of the fermentation, the resulting biomass is separated from the culture medium, preferably by centrifugation or filter-pressing, until a dry residue is obtained, preferably at 105° C. of from 20 to 25% (weight/weight). If necessary, the bacterial biomass can be kept in the fermenter for another 24 hours at a temperature of 10-15° C. in the absence of aeration and stirring.

The bacterial biomass can be stored in a freezer at −20° C., or lyophilized and stored also at room temperature, not higher than 30° C.

In particular, after the fermentation process, in order to carry out the separation of the biomass, the fermentation broth must be brought to a temperature of at least 10-30° C., preferably of between 15 and 20° C., in order to start the flocculation step.

The biomass is in a colloidal suspension, i.e., in a state in which the microorganisms are finely dispersed in a liquid medium; the liquid medium in this case is the exhausted nutrient broth which may, in the long run, deteriorate the quality of the microorganism. The separation of the biomass takes place after first adding a cationic solution, preferably 10%, followed by an anionic solution, preferably 0.1%. The amount of cationic solution added can range from 2 to 8% with respect to the mass to be flocculated, while the anionic solution ranges from 1 to 2.5%. Preferably, the cationic solution ranges from 4 to 7%, while the anionic solution ranges from 1 to 2%. Preferably, the suspension is kept under stirring.

The low molecular weight cationic flocculant acts as a coagulant and in a few minutes a micro flocculant is formed.

The anionic solution is then added.

The newly formed micro flocculant serves as a substrate for the subsequent agglomeration of the high molecular weight anionic flocculant.

Following the addition of the anionic solution, usually after 10 minutes the flocculant is completely formed and can be separated by centrifugation or by filter-pressing.

Generally, the separation takes place by the use of filters having pores with a diameter $\geq 0.45$ μm. If it is deemed appropriate, the filtered biomass can be resuspended in 1/5 of demineralized water with respect to the initial suspension mass and then filtration is repeated; in this way, the biomass is further cleaned from the broth culture residues.

If it is stored as a paste, the biomass is usually mixed with a preservative, preferably sulfate or ammonium salt.

In industrial-scale separation processes, double-sheet panels or auto-drainage centrifuges can be used.

The biomass obtained with the method described above consists of bacterial cells of the *Rhodococcus biphenylivorans* Palladio 22 strain exhibiting a high nitrile hydratase activity that allows the hydration of aliphatic and aromatic nitriles, thereby obtaining the corresponding amides, in particular acrylamide.

For the acrylamide production reaction, 1 g/3 L of dry biomass of bacterial cells of *Rhodococcus biphenylivorans* Palladio 22, obtained as indicated in the culture method described, is resuspensed in about one liter of demineralized water in a reactor maintained at an initial reaction temperature of between 10 and 17° C., preferably 13-15° C. Some additive in solution may be added to the initial aqueous solution.

Within the reactor, the acrylamide production process takes place at a temperature range of between 10 and 27° C., preferably between 14 and 23° C., and a pH of between 5.0 and 8.5, preferably between 6.8 and 7.2.

The synthesis of acrylamide begins when acrylonitrile is added to the aqueous solution containing the biomass of *Rhodococcus biphenylivorans* Palladio 22.

The addition of acrylonitrile can be done continuously or in steps so that, during the reaction of conversion to acrylamide, its free concentration in solution is never greater than 0.8%, preferably 0.6%, preferably 0.5%, even more preferably 0.4 or 0.3% with respect to the total weight of the reaction solution.

During the reaction, the suspension is kept under constant stirring between 50 and 200 rpm, preferably between 100 and 150 rpm. This stirring range may vary depending on the size of the reactor and the type of stirrer used.

The concentrations of acrylonitrile and acrylamide in the reaction solution are constantly monitored by spectrophotometric, refractometric and gas-chromatographic measurements until the whole amount of acrylonitrile required for the reaction is added, or until the desired concentration of acrylamide is achieved.

The process is in any case stopped when the bioconversion action carried out by the nitrile hydratase enzyme is almost null. This can occur when a high concentration of acrylamide is achieved.

The hydration reaction is blocked by stopping the addition of acrylonitrile and/or upon reaching the predetermined acrylamide concentration.

The final product formed by acrylamide in aqueous solution and suspended biomass contains acrylamide in a concentration obtainable from 30 to 57.5%, preferably from 45 to 57%, from 48 to 56%, from 50% to 54%. The concentration of acrylamide is measured by appropriate instruments, such as gas chromatograph, HPLC, refractometer and spectrophotometer.

In particular, acrylamide production yields up to a concentration of 57.5% (w/w) in aqueous solution can be achieved.

At the end of the reaction using gas chromatography, the absence of contaminating residues of acrylonitrile is checked and the suspension of acrylamide and biomass is subjected to appropriate purification treatments, for example by filtration or centrifugation to separate the biocatalyst from acrylamide in aqueous solution.

The acrylamide separation process preferably takes place by automatic centrifugation.

The resulting acrylamide is usually stored in compliance with specific safety rules into stainless steel tanks or vessels with continuous recirculating air at a temperature of 20° C.

During storage for prolonged periods of time, acrylamide can undergo polymerization phenomena and for this reason the concentration of polymers, that must have a value of ≥15 FTU (turbidimetric formazine units) is constantly monitored.

In order to inhibit the polymerization, the solution containing acrylamide can be blown with air before being transferred to storage.

The final solution is transparent and free of residues of biocatalyst in suspension.

A man skilled in the art will appreciate that the method described in the invention may be adapted for large-scale production, using industrial fermenters and reactors with larger volumes.

According to an embodiment variant of the invention, the synthesis of acrylamide takes place by the addition of acrylonitrile to the biomass of Palladio 22 strain immobilized on a solid substrate per se known, such as activated carbon, silicates, zeolites, cross-linked acrylamide, polymeric substrates, etc.

Moreover, it is possible, according to known techniques, to immobilize on solid substrates, such as the substrates mentioned above, the nitrile hydratase enzyme extracted from the bacterial strain of the invention and synthesize acrylamide by the addition of acrylonitrile to the above enzyme immobilized on substrate.

Advantageously, such methods allow both producing acrylamide "continuously", thereby increasing the yield of the reaction, and facilitating the removal of the biocatalyst from the finished acrylamide, thus reducing the time required to carry out the process itself.

Also the bacterial strains of *Rhodococcus biphenylivorans* obtainable by reproduction or multiplication of the bacterial strain *Rhodococcus biphenylivorans* named Palladio 22 of the present invention are intended to be protected by the present invention. These strains are used for the production of amides, in particular for the production of acrylamide, as described above. Moreover, the growth of the above bacterial strains is obtained using a culture method according to the technical features described for the strain of the invention. These bacterial strains have excellent growth characteristics in culture and are capable of catalyzing the hydrolysis of aliphatic and aromatic nitriles in the corresponding amide.

It is not excluded that, according to different embodiment variants of the invention, such bacterial strains have spontaneous gene mutations that occur naturally in cultured growth, due to the high genetic variability that characterizes the bacteria and allows them to adapt to different growth environments.

It is also possible that these gene mutations could be induced mutations caused by the use of external chemical, physical or biological agents in the culture, such as antibiotics, UV rays or viruses, as long as the bacterial strains having such mutations, derived from the multiplication/reproduction of the Palladio 22 strain, are suitable for being used with a use or a method as described above and have the same technical features of the invention strain.

The invention and the advantages thereof will become apparent from the following illustrative examples.

The following examples describe, for illustrative and non-limiting purposes only, the various steps required to carry out the invention.

EXAMPLE 1

Preparation and Seeding on Petri Dishes

The cells of the *Rhodococcus biphenylivorans* Palladio 22 strain are grown on Petri dishes prepared with generic growth medium having the following composition: 1.0 g/L bovine extract, 2.0 g/L yeast extract, 5.0 g/L Peptone, 5.0 g/L NaCl, to which agar is added to a final concentration of 1.5%. The pH of the solution is corrected if necessary with NaOH or $H_3PO_4$ to a value of 7.0±0.1.

Once prepared, the broth is brought to a boil to favor the complete solubilization of agar. The same then undergoes a process of sterilization at a temperature of 121° C. for 15 minutes. After sterilization, under sterile laminar flow hood, the broth is poured into sterile Petri dishes where it will be made to gelify.

The Petri dishes are seeded with the bacterial strain using a sterile loop and placed in an incubator for 3 days at a temperature of 30° C. in aerobiosis.

After incubation, pink-orange pigmented colonies with circular and convex shape form on the surface of the culture medium.

EXAMPLE 2

Preparation and Seeding of Slants

The colonies of *Rhodococcus biphenylivorans* Palladio 22 thus obtained are grown in slants filled with the same medium used in the Petri dishes.

The slants tubes undergo a sterilization step at a temperature of 121° C. for 15 minutes.

After the sterilization process, the tubes are positioned in the incubator in inclined position so as to obtain, as a result of the solidification of the culture medium, an inclined surface of the slant.

The slants are then seeded, using a sterile loop, with colonies derived from the previous growth step and placed in an incubator for 2 days at a temperature of 30° C.

EXAMPLE 3

Seeding of the Strain in Liquid Medium in Flask

The biomass of bacterial cells obtained by growth in the slants is resuspended in sterile saline with pH 7.2 at 30° C.

This biomass suspension is then used for the inoculation of a flask containing a generic liquid medium supplemented with yeast extract at a concentration of 15 g/L, or in a synthetic medium having the following composition (g/L):

| | |
|---|---|
| $Na_2HPO_4 \times 12\ H_2O$ | 4.8 |
| $KH_2PO_4$ | 1.4 |
| Urea | 8 |
| Sugar | 20 |
| $CoCl_2 \times 6\ H_2O$ | 0.015 |
| $MgSO_4 \times 7\ H_2O$ | 0.9 |
| $ZnSO_4 \times 7\ H_2O$ | 0.3 |
| $Ca^{2+}$ salt | 0.4 |
| $FeSO_4 \times 7H_2O$ with chelating agent | 0.02 |
| Yeast extract | 3 |
| Demineralized water | at 1 L |

The biomass is inoculated in the flask under sterile conditions and growth takes place at a temperature of 30° C. and a pH of 7.2. The strain growth in liquid phase takes place in an orbital shaker that stirs the flasks at 300 rpm.

The biomass growth in the flask is blocked at an optical density of 35-38 OD, measured at 540 nm wavelength in a cell having a 10 mm thickness.

The resulting bacterial suspension is used for inoculations in the subsequent scale-up step in fermenter.

EXAMPLE 4

Growth of the Strain in Liquid Medium in Fermenter and Subsequent Scale-Up

The culture medium having the following composition (g/L) is prepared in a 20 L fermenter:

| | |
|---|---|
| $Na_2HPO_4 \times 12\ H_2O$ | 4.8 |
| $KH_2PO_4$ | 1.4 |
| Urea | 12 |
| Sugar | 70 |
| $CoCl_2 \times 6\ H_2O$ | 0.05 |
| $MgSO_4 \times 7\ H_2O$ | 1 |
| $ZnSO_4 \times 7\ H_2O$ | 0.2 |
| $Ca^{2+}$ salt | 0.3 |
| $FeSO_4 \times 7H_2O$ with chelating agent | 0.04 |
| Anti-foaming agent | 0.3 |
| Yeast extract | 4 |
| Demineralized water | at 1 L |

The culture medium is sterilized at 121° C. for 15 min. and then cooled down to 30° C. prior to the inoculation of the bacterial culture.

The volume of the inoculum is equal to ⅟50 with respect to the final volume of culture medium contained in the fermenter.

The growth conditions in the 20 L fermenter involve aeration of 5-10 L/min, stirring from 150 to 400 rpm, variable depending on the biomass concentration, $pO_2 \leq 55\%$, temperature of 30° C. and a pH of between 6.5 and 7.4 (varies during growth) until an optical density of 170-190 OD is achieved.

In order to determine when to block the bacterial growth, optical density and nitrile hydratase activity parameters are evaluated which should have values of between 90-220 OD and at least 150 μmoles amide/min/mg dry weight cells, respectively.

For the subsequent scale-up steps, the growth process maintains the same characteristics, but 400/1000 L and 20000/50000 L fermenters are used in a sequence.

The final biomass thus obtained is separated by centrifugation or filter-pressing from the culture medium and stored in a freezer at −20° C., or lyophilized and stored at a room temperature not greater than 30° C.

If necessary, before the separation process, the bacterial culture can be kept under culture conditions for another 24 hours at a temperature of 10-15° C., and in the absence of air and stirring.

EXAMPLE 5

Flocculation and Separation of the Biomass

The scale-up steps of the fermentation of *Rhodococcus biphenylivorans* Palladio 22 strain were carried out as described in example 4.

At the end of the last fermentation, the bacterial suspension is brought to a temperature of at least 15° C. before starting the flocculation process.

In order to carry out the separation of the biomass that is in a colloidal suspension, flocking solutions are added to the culture broth.

In particular, considering an amount of 500 g, 25 mL of a 10% cationic solution are added to the bacterial suspension under stirring at 50 rpm which after few minutes leads to the formation of a microflocculant.

Thereafter, 8 mL of a 0.1% anionic solution are added slowly, keeping the suspension under stirring up to the complete formation of flakes.

At the end of the reaction, the final separation step of the biomass from the exhausted broth is carried out through the use of filters having pores with a diameter≥0.45 μm.

The resulting biomass is then resuspended in 100 g of $H_2O$ to be then refiltered. This operation drastically reduces the residues of culture broth.

The resulting biomass is stored as a paste at −20° C., or lyophilized and stored at room temperature not greater than 30° C.

EXAMPLE 6

Acrylamide Production Reaction

For the acrylamide production reaction, 1 g (dry weight) of biomass of *Rhodococcus biphenylivorans* Palladio 22 is resuspended in an aqueous solution in a cooled reactor with a total volume of 3 L.

The acrylamide production process takes place under constant stirring (150 rpm) at temperature ranging from 14 to 23° C., pH of 7.0±0.2 and a concentration of free acrylonitrile in solution never exceeding 0.5%.

To 1201.26 g water mass and biocatalyst are added 798.74 g of acrylonitrile, either continuously or in steps, up to the complete conversion of acrylonitrile into 1070 g of acrylamide (100%).

When the speed of the nitrile hydratase enzyme decreases drastically, the reaction is stopped. Usually this phenomenon may happen when the concentration of acrylamide is above 53%.

The acrylamide produced is separated from the biomass by automatic centrifugation and stored in special tanks or containers.

The final concentration in solution of acrylamide produced is 53.5% and is free from acrylonitrile residues.

EXAMPLE 7

Acrylamide Production Reaction

For the acrylamide production reaction, 1 g (dry weight) of biomass of *Rhodococcus biphenylivorans* Palladio 22 is resuspended in an aqueous solution in a cooled reactor with a total volume of 3 L.

The acrylamide production process takes place under constant stirring (150-200 rpm) at temperature ranging from 14 to 23° C., pH of 7.0±0.2 and a concentration of free acrylonitrile in solution not greater than 0.5-0.8%.

To 1141.55 g water mass and biocatalyst are added 858.45 g of acrylonitrile, either continuously or in steps, up to the complete conversion of acrylonitrile into 1150 g of acrylamide (100%).

When the speed of the nitrile hydratase enzyme decreases drastically, the reaction is stopped. Usually this phenomenon may happen when the concentration of acrylamide is above 53%. The reaction batch for this concentration is completed in about 4-8 hours.

The acrylamide produced is separated from the biomass by automatic centrifugation and stored in special tanks or containers.

The final concentration in solution of acrylamide produced is 57.5% and is free from acrylonitrile residues.

The invention claimed is:

1. A method for producing acrylamide, comprising:
hydrating acrylonitrile in an aqueous solution using a biomass consisting essentially of a bacterium *Rhodococcus biphenylivorans* strain Palladio 22, registered at Belgian Coordinated Collections of Microorganisms-Laboratorium voor Microbiologie, Universiteit Gent (BCCM-LMG) under registration number LMG P-29520,
wherein said hydrating the acrylonitrile yields acrylamide at a concentration between 30 to 57.5% (weight/weight) of the aqueous solution.

2. The method according to claim 1, wherein the biomass is in a form of dried, lyophilized, or paste biomass having a dry residue from 18 to 30% (weight/weight) prior to hydrating the acrylonitrile in the aqueous solution using said biomass.

3. The method according to claim 1, comprising adding the acrylonitrile to the aqueous solution to a concentration of acrylonitrile that is less than 0.8% of a total weight of the aqueous solution.

4. The method according to claim 3, wherein the concentration of acrylamide yielded from hydrating the acrylonitrile is between 50 and 57.5% (weight/weight).

5. The method according to claim 3, wherein the concentration of acrylamide yielded from hydrating the acrylonitrile is between 50 and 54% (weight/weight).

6. The method according to claim 3, wherein said hydrating acrylonitrile takes place in a temperature range of between 14 and 23° C. and at a pH of between 5.0 and 8.5.

7. The method according to claim 1, further comprising immobilizing said biomass on a solid substrate.

8. The method according to claim 1, further comprising extracting a nitrile hydratase enzyme from said biomass and immobilizing said nitrile hydratase enzyme on a solid substrate.

9. The method according to claim 1, further comprising obtaining the biomass used for hydrating acrylonitrile in the aqueous solution, wherein said bacterium *Rhodococcus biphenylivorans* strain Palladio 22 LMG P-29250 is cultured on a nutrient medium comprising: a phosphate buffer solution comprising sodium and potassium, a carbon source, a nitrogen source, a magnesium salt, a zinc salt, a calcium salt, an iron salt (II), a cobalt salt and, optionally, a yeast extract.

10. The method according to claim 9, wherein the bacterium is cultured at a temperature of 10-35° C., for 2-4 days, and at a growth pH of between 8.3-6.3.

11. The method according to claim 9, comprising: a step of growing the bacterium on a solid medium, a step of growing the bacterium in a liquid medium, a fermentation step, a step of flocculation, and a step of separating the biomass.

12. The method according to claim 9, wherein the bacterium is cultured until the nutrient medium has an optical density of between 90-220 OD measured by a 540 nm wavelength spectrophotometer in a cell having a thickness of 10 mm.

13. The method according to claim 9, wherein the biomass has a nitrile hydratase activity of at least 150 μmoles of amide/min/mg dry weight cells of the biomass.

14. The method according to claim 1, wherein the concentration of acrylamide yielded from hydrating the acrylonitrile is between 50% to 57.5% (weight/weight) of the aqueous solution.

* * * * *